United States Patent
Hovland et al.

(10) Patent No.: US 9,394,228 B2
(45) Date of Patent: Jul. 19, 2016

(54) METHODS OF TREATMENT USING LIPID COMPOUNDS

(75) Inventors: Ragnar Hovland, Nesoddtangen (NO); Tore Skjæret, Oslo (NO); David Fraser, Blommenholm (NO)

(73) Assignee: PRONOVA BIOPHARMA NORGE AS, Lysaker (NO)

( * ) Notice: Subject to any disclaimer, the term of this patent is extended or adjusted under 35 U.S.C. 154(b) by 48 days.

(21) Appl. No.: 13/883,405

(22) PCT Filed: Nov. 3, 2011

(86) PCT No.: PCT/IB2011/002925
§ 371 (c)(1),
(2), (4) Date: Sep. 6, 2013

(87) PCT Pub. No.: WO2012/059818
PCT Pub. Date: May 10, 2012

(65) Prior Publication Data
US 2013/0345269 A1 Dec. 26, 2013

Related U.S. Application Data

(60) Provisional application No. 61/410,445, filed on Nov. 5, 2010.

(51) Int. Cl.
| | | |
|---|---|---|
| C07C 69/734 | (2006.01) |
| C07D 263/26 | (2006.01) |
| C07C 59/60 | (2006.01) |
| A61K 31/19 | (2006.01) |
| A61K 31/355 | (2006.01) |

(52) U.S. Cl.
CPC .............. *C07C 69/734* (2013.01); *A61K 31/19* (2013.01); *A61K 31/355* (2013.01); *C07C 59/60* (2013.01); *C07D 263/26* (2013.01)

(58) Field of Classification Search
None
See application file for complete search history.

(56) References Cited

U.S. PATENT DOCUMENTS

| | | |
|---|---|---|
| 2,909,554 A | 10/1959 | Doerr |
| 4,009,211 A | 2/1977 | Onopchenko et al. |
| 4,032,564 A | 6/1977 | Henrick et al. |
| 4,040,781 A | 8/1977 | Lamberti et al. |
| 4,209,410 A | 6/1980 | Baldwin |
| 4,214,088 A | 7/1980 | Abeler et al. |
| 4,286,053 A | 8/1981 | Ishikawa et al. |
| 4,297,268 A | 10/1981 | Abeler et al. |
| 4,368,190 A | 1/1983 | Shen et al. |
| 4,411,808 A | 10/1983 | Gutierrez et al. |
| 4,444,766 A | 4/1984 | Bosies et al. |
| 5,306,754 A | 4/1994 | Yamamoto et al. |
| 5,328,953 A | 7/1994 | Lynch |
| 5,447,820 A | 9/1995 | Hayakawa et al. |
| 5,523,430 A | 6/1996 | Patel et al. |
| 5,612,093 A | 3/1997 | Braig et al. |
| 5,763,517 A | 6/1998 | Yamamoto et al. |
| 5,770,584 A | 6/1998 | Kucera et al. |
| 5,990,173 A | 11/1999 | Patoiseau et al. |
| 6,060,515 A | 5/2000 | Elias et al. |
| 6,365,628 B1 | 4/2002 | Berge |
| 6,376,688 B1 | 4/2002 | Ferrante et al. |
| 6,511,670 B1 | 1/2003 | Maignan et al. |
| 6,624,190 B2 | 9/2003 | Khoury et al. |
| 6,723,717 B1 | 4/2004 | Youngquist et al. |

(Continued)

FOREIGN PATENT DOCUMENTS

| | | |
|---|---|---|
| CA | 2115345 | 2/1993 |
| CA | 2667211 | 5/2008 |

(Continued)

OTHER PUBLICATIONS

Matsumoto et al. (Atherosclerosis vol. 197, Issue 2, Apr. 2008, pp. 524-533).*
International Search Report for International Application No. PCT/IB2011/002925, dated Mar. 5, 2012.
Flock, S. et al., "Syntheses of Some Polyunsaturated Sulfur- and Oxygen-containing Fatty Acids Related to Eicosapentaenoic and Docosahexaenoic Acids," *Acta Chemica Scandinavica* (1999) 53:436-445.

(Continued)

*Primary Examiner* — Jeffrey S Lundgren
*Assistant Examiner* — William Lee
(74) *Attorney, Agent, or Firm* — Finnegan, Henderson, Farabow, Garrett & Dunner, L.L.P.

(57) ABSTRACT

Methods are disclosed to treat or prevent at least one disease or condition in a subject in need thereof comprising administering a compound of Formula (I):

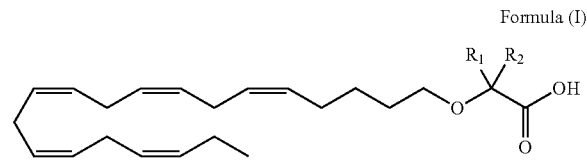

Formula (I)

or a pharmaceutically acceptable salt, or ester thereof, wherein $R_1$ and $R_2$ are independently chosen from a hydrogen atom or linear, branched, and/or cyclic $C_1$-$C_6$ alkyl groups, with the proviso that $R_1$ and $R_2$ are not both hydrogen or a pharmaceutically acceptable salt or ester thereof. Such diseases or conditions may relate to coronary heart disease (CHD), for example atherosclerosis; metabolic syndrome/insulin resistance; and/or a dyslipidemic condition such as hypertriglyceridemia (HTG), elevated LDL-cholesterol, elevated total-cholesterol, elevated Apo B and low HDL-cholesterol.

The present disclosure further provides for a method of reducing atherosclerosis development. Pharmaceutical compositions comprising a compound of Formula (I) are also disclosed.

19 Claims, 4 Drawing Sheets

(56) References Cited

U.S. PATENT DOCUMENTS

| | | | |
|---|---|---|---|
| 7,250,456 | B2 | 7/2007 | Eigen et al. |
| 7,273,852 | B2 | 9/2007 | Tsuji et al. |
| 7,427,583 | B2 | 9/2008 | Couillet et al. |
| 7,517,858 | B1 | 4/2009 | Hostetler et al. |
| 7,902,399 | B2 | 3/2011 | Berge et al. |
| 7,968,617 | B2 | 6/2011 | Thalacker et al. |
| 8,173,831 | B2 | 5/2012 | Milne et al. |
| 8,304,551 | B2 | 11/2012 | Milne et al. |
| 8,735,436 | B2 * | 5/2014 | Hovland et al. ............... 514/376 |
| 8,741,966 | B2 | 6/2014 | Holmeide |
| 8,759,558 | B2 | 6/2014 | Holmeide et al. |
| 2003/0147814 | A1 | 8/2003 | Scherrer et al. |
| 2004/0126424 | A1 | 7/2004 | Jandacek et al. |
| 2005/0107503 | A1 | 5/2005 | Couillet et al. |
| 2006/0135785 | A1 | 6/2006 | Patoiseau et al. |
| 2006/0247458 | A1 | 11/2006 | Yamamoto et al. |
| 2007/0060497 | A1 | 3/2007 | Krahmer et al. |
| 2007/0088170 | A1 | 4/2007 | Bryhn et al. |
| 2007/0167529 | A1 | 7/2007 | Walton et al. |
| 2007/0254862 | A1 | 11/2007 | Antel et al. |
| 2009/0137567 | A1 | 5/2009 | Perrine et al. |
| 2010/0267828 | A1 * | 10/2010 | Holmeide et al. ............ 514/549 |
| 2010/0280109 | A1 | 11/2010 | Holmeide |
| 2011/0190395 | A1 | 8/2011 | Holmeide et al. |
| 2012/0122940 | A1 | 5/2012 | Hovland et al. |
| 2012/0252850 | A1 | 10/2012 | Milne et al. |
| 2012/0264791 | A1 | 10/2012 | Milne et al. |
| 2013/0046013 | A1 | 2/2013 | Hovland et al. |
| 2014/0221439 | A1 | 8/2014 | Hovland et al. |
| 2014/0316002 | A1 | 10/2014 | Holmeide et al. |

FOREIGN PATENT DOCUMENTS

| | | |
|---|---|---|
| CA | 2667150 | 11/2008 |
| CN | 1248916 A | 3/2000 |
| CN | 101213281 A | 7/2008 |
| CN | 101225064 | 7/2008 |
| CN | 101213281 B | 3/2013 |
| EP | 0 002 007 | 5/1979 |
| EP | 0 050 327 | 4/1982 |
| EP | 0 175 591 | 3/1986 |
| EP | 0 399 183 | 11/1990 |
| EP | 0 463 947 | 1/1992 |
| EP | 2 248 798 | 11/2010 |
| GB | 1038723 | 8/1966 |
| GB | 1523276 | 8/1978 |
| JP | 48-039001 B | 11/1973 |
| JP | 04-051149 | 2/1992 |
| JP | 11-180929 | 7/1999 |
| JP | 2000 344736 A | 12/2000 |
| JP | 2003 527364 T | 9/2003 |
| WO | WO 97/38688 | 10/1997 |
| WO | WO 98/32444 | 7/1998 |
| WO | WO 00/72920 | 12/2000 |
| WO | WO 01/68582 | 9/2001 |
| WO | WO 01/98328 | 12/2001 |
| WO | WO 03/014073 | 2/2003 |
| WO | WO 03/063878 | 8/2003 |
| WO | WO 2005/073164 | 8/2005 |
| WO | WO 2006/025246 | 3/2006 |
| WO | WO 2006/094915 | 9/2006 |
| WO | WO 2006/117664 | 11/2006 |
| WO | WO 2006/117668 | 11/2006 |
| WO | WO 2007/116027 | 10/2007 |
| WO | WO 2008/053331 | 5/2008 |
| WO | WO 2008/053340 | 5/2008 |
| WO | WO 2008/125241 | 10/2008 |
| WO | WO 2009/056983 | 5/2009 |
| WO | WO 2009/061208 | 5/2009 |
| WO | WO 2009/061208 | 12/2009 |
| WO | WO 2009/149496 | 12/2009 |
| WO | WO 2009/156621 | 12/2009 |
| WO | WO 2010/006085 | 1/2010 |
| WO | WO 2010/008299 | 1/2010 |
| WO | WO 2010/128401 | 11/2010 |
| WO | WO 2011/089529 | 7/2011 |
| WO | WO 2012/059818 | 5/2012 |
| WO | WO 2012/115695 | 8/2012 |
| WO | WO 2013/016531 | 1/2013 |

OTHER PUBLICATIONS

Ahmad, J. et al., "Reactions in Monolayers: Base-Catalyzed Ester Hydrolysis Revisited," *Langmuir* (1990) 6:1797-1799.

Berge, S.M. et al., "Pharmaceutical Salts," *J. Pharmaceutical Sciences* (1977) 66(1):1-19.

Brain, E.G. et al., "Derivatives of 6-Aminopenicillanic Acid. Part II.* Trisubstituted Acetyl Derivatives," *J. Chemical Society* (1962) 1445-1453.

Burness, D.M. "Decarboxylation of Thietin Salts," *J. Organic Chemistry*, (1959) 24(6):849-852.

Co-pending U.S. Appl. No. 13/574,132, filed Jul. 19, 2012.

Co-pending U.S. Appl. No. 14/250,980, filed Apr. 11, 2014.

Co-pending U.S. Appl. No. 14/263,793, filed Apr. 28, 2014.

Derzhinskii, A.R. et al., "Functional Sulfur-Containing Compounds. 4. Preparation of Chloro(Bromo)Alkyl Sulfones by Oxidative Halogenation of Hydroxyalkyl Sulfides and Sulfoxides with Mixtures of Hydrogen Peroxide and a Hydrohalic Acid," *Bulletin of the Academy of Sciences of the USSR* (1982) 31(5):995-1001.

Ferrell, W.J. et al., "Synthesis and Properties of $^{35}$S, $^{14}$C and $^{3}$H Labeled S-Alkyl Glycerol Ethers and Derivatives," *Chemistry & Physics of Lipids* (1976) 16:276-284.

Ferrucci, L. et al., "Relationship of Plasma Polyunsaturated Fatty Acids to Circulating Inflammatory Markers," *J. Clin. Endocrin. & Metab.* (2006) 91(2):439-446.

Geleijnse, J.M. et al., "Blood Pressure Response to Fish Oil Supplementation: Metaregression Analysis of Randomized Trials," *J. Hypertension* (2002) 20(8):1493-1499.

Goldsworthy, L.J. et al., "Some Sulphides Containing the 2-Chloroethyl Group," *J. Chemical Society* (1948) 2177-2179.

Granlund, L. et al., "Effects of Structural Changes of Fatty Acids on Lipid Accumulation in Adipocytes and Primary Hepatocytes," *Biochimica et Biophysica Acta* (2005) 1687:23-30.

Grupp, I.L. et al., "Protection Against Hypoxia-Reoxygenation in the Absence of Poly (ADP-Ribose) Synthetase in Isolated Working Hearts," *J. Mol. Cell Cardiol.* (1999) 31:297-303.

Heckmann, B. et al., "Grignard Additions to α,β-Unsaturated Dioxolanones: Preparation of Chiral Allylic Alcohols and Protected α-Hydroxy Aldehydes," *Tetrahedron Letters* (1996) 37:1421-1424.

Hermetter, A. & Paltauf, F., "A Facile Procedure for the Synthesis of Saturated Phosphatidylcholines," *Chemistry & Physics of Lipids* (1981) 28:111-115.

Hill, A.J. & Fager, E.W., "Some α-Alkylthio Aliphatic Acids," *J. American Chemical Society* (1943) 65(12):2300-2301.

Holmeide, A.K. & Skattenbol, L., "Syntheses of Some Polyunsaturated Trifluoromethyl Ketones as Potential Phospholipase $A_2$ Inhibitors," *J. Chem. Soc., Perkin Trans.* (2000) 1:2271-2276.

Hosokawa, M. et al., "Preparation of Therapeutic Phospholipids Through Porcine Pancreatic Phospholipase $A_2$-Mediated Esterification and Lipozyme-Mediated Acidolysis," *J. Am. Oil Chem. Soc.* (1995) 72(11):1287-1291.

International Search Report for International Application No. PCT/IB2010/001251, dated Oct. 4, 2010.

International Search Report for International Application No. PCT/IB2011/000250, dated May 31, 2011.

International Search Report for International Application No. PCT/N02008/000391, dated Feb. 4, 2009.

International Search Report for International Application No. PCT/N02009/000262, dated Oct. 23, 2009.

Jones, P.B. et al., "A New Class of Antituberculosis Agents," *J. Med. Chem.* (2000) 43:3304-3314.

Kameyama, E. et al., "Alkylcarboxymethyl Sulphoxides," *American Chemical Society Chemical Abstracts* (1971) 74(23):401.

Kasai, Y. et al., "Synthesis of Diphenylalkane Sulfonate and Its Surface Activity," *Kogyo Kagaku Zasshi* (1965) 68(11):2073-2077.

Lamango, N.S. et al., "Inhibition Mechanism of S-Adenosylmethionine-Induced Movement Deficits by Prenylcysteine Analogs," *Pharmacology, Biochemistry, & Behavior* (2003) 76:433-442.

(56) References Cited

OTHER PUBLICATIONS

Larsen, L.N. et al., "α- and β- Alkyl-Substituted Eicosapentaenoic Acids: Incorporation into Phospholipids and Effects on Prostaglandin H Synthase and 5-Lipoxygenase," *Biochemical Pharmacology* (1998) 55:405-411.

Larsen, L.N. et al., "Polyunsaturated Thia- and Oxa-Fatty Acids: Incorporation into Cell-Lipids and Their Effects on Arachidonic Acid- and Eicosanoid Syntheses," *Biochimica et Biophysica Acta* (1997) 1348:346-354.

Larsen, L.N. et al., "Sulfur-Substituted and α-Methylated Fatty Acids as Peroxisome Proliferator-Activated Receptor Activators," *Lipids* (2005) 40(1):49-57.

Lilja-Hallberg, M. & Härröd, M., "Enzymatic Esterification of Long Polyunsaturated Fatty Acids and Lyso-Phosphatidylcholine in Isooctane and Ethanol," *Biocatalysis* (1994) 9:195-207.

Livingston, J.R. & Drogin, R., "The Synthesis and Some Surface Active Properties of Alkylthioalkyl and Alkoxyalkyl Sulfates," *J. American Oil Chemists' Society* (1965) 42:720-723.

Másson, M. et al., "Marine Lipids for Prodrugs, Soft Compounds and Other Pharmaceutical Applications," *Pharmazie* (2000) 55(3):172-177.

Matsumoto, M. et al., "Orally Administered Eicosapentaenoic Acid Reduces and Stabilizes Atherosclerotic Lesions in ApoE-Deficient Mice," *Atherosclerosis* (2008) 197:524-533.

Meyer, K.L. et al., "In Vitro Evaluation of Phosphocholine and Quaternary Ammonium Containing Lipids as Novel Anti-HIV Agents," *J. Med. Chem.* (1991) 34(4):1377-1383.

Notice of Allowance in U.S. Appl. No. 12/741,890, issued Jan. 17, 2014.

Notice of Allowance in U.S. Appl. No. 13/054,212, issued Jan. 29, 2014.

Notice of Allowance in U.S. Appl. No. 13/319,101, issued Jan. 13, 2014.

Nystrom, R.F. & Brown, W.G., "Reduction of Organic Compounds by Lithium Aluminum Hydride. II. Carboxylic Acids," *J. American Chemical Society* (1947) 69(10):2548-2549.

Office Action from U.S. Appl. No. 12/741,890, dated Aug. 3, 2012.
Office Action from U.S. Appl. No. 12/741,890, dated Dec. 10, 2012.
Office Action from U.S. Appl. No. 12/741,890, dated Aug. 6, 2013.
Office Action from U.S. Appl. No. 13/054,212, dated Apr. 1, 2013.
Office Action from U.S. Appl. No. 13/054,212, dated Jul. 1, 2013.
Office Action from U.S. Appl. No. 13/319,101, dated Jan. 31, 2013.
Office Action from U.S. Appl. No. 13/319,101, dated Apr. 24, 2013.
Office Action from U.S. Appl. No. 13/319,101, dated Oct. 2, 2013.

Okoronkwo, A.E. et al., "Synthesis of ω-Hydroxy-α-Alkyl/Aryl-γ-Organo-Selenium and γ-Organo-Tellurium: A New Class of Organochalcogen Compounds with Antinociceptive Activity," *Tetrahedron Letters* (2008) 49:3252-3256.

Parkkari, T. et al., "α-Methylated Derivatives of 2-Arachidonoyl Glycerol: Synthesis, CB1 Receptor Activity, and Enzymatic Stability," *Bioorg. & Med. Chem. Lett.* (2006) 16:2437-2440.

Pitt, M.J. et al., "Synthesis of Polyunsaturated β-Oxa Fatty Acids Via Rhodium Mediated Carbenoid Insertion," *Synthesis* (1997) 7:1240-1242.

Registry Copyright 2008 ACS on STN (RN 785712-42-7, 714185-72-5, 45247-37-8).

Rossmeisl, M. et al., "Prevention and Reversal of Obesity and Glucose Intolerance in Mice by DHA Derivatives," *Obesity* (2009) 17(5):1023-1031.

Shchepin, R. et al., "Quorum Sensing in *Candida albicans*: Probing Farnesol's Mode of Action with 40 Natural and Synthetic Farnesol Analogs," *Chemistry & Biology* (2003) 10:743-750.

Shirley, D.A. et al., "Alkylation with Long Chain *p*-Toluenesulfonates. IV. Alkylation of Alcohols and Amines with *n*-Octadecyl *p*-Toluenesulfonate," *J. Organic Chemistry* (1953) 18:378-381.

Silverman, R.B., The Organic Chemistry of Drug Design and Drug Action 4, 14-28 (Academic Press 1992).

Simopoulos, A.P., "Essential Fatty Acids in Health and Chronic Disease," *Am. J. Clin. Nutr.* (1999) 70(Suppl):560S-569S.

Srisiri, W. et al., "Syntheses of Polymerizable Monoacylglycerols and 1,2-Diacyl-*sn*-Glycerols," *J. Org. Chem.* (1996) 61(16):5911-5915.

Stahl, P.H. & Wermuth, C.G., eds., "Chapter 12: Monographs on Acids and Bases" 265-327, in Handbook of Pharmaceutical Salts: Properties, Selection, and Use.

Supplementary European Search Report for European Patent Application No. 11 83 7647, dated Feb. 13, 2014.

Togashi, N. et al., "Antibacterial Activity of Long-Chain Fatty Alcohols Against *Staphylococcus aureus*," *Molecules* (2007) 12:139-148.

Tran, P.O.T. et al., "Inhibition of Interleukin-1β-Induced COX-2 and EP3 Gene Expression by Sodium Salicylate Enhances Pancreatic Islet β-Cell Function," *Diabetes* (2002) 51:1772-1778.

Tsotinis, A. et al., "Synthesis and Antiretroviral Evaluation of New Alkoxy and Aryloxy Phosphate Derivatives of 3'-Azido-3'-Deoxythymidine," *J. Med. Chem.* (1996) 39:3418-3422.

Udding, J. et al., "Xanthate Transfer Cyclization of Glycolic Acid-Derived Radicals. Synthesis of Five- to Eight-Membered Ring Ethers," *J. Org. Chem.* (1994) 59:6671-6682.

Vaagenes, H. et al., "Methylated Eicosapentaenoic Acid and Tetradecylathioacetic Acid: Effects on Fatty Acid Metabolism," *Biochem. Pharmacol.* (1999) 58:1133-1143.

Wang, P. et al., "Synthesis of Phospholipid-Inhibitor Conjugates by Enzymatic Transphosphatidylation with Phospholipase D," *J. Am. Chem. Soc.* (1993) 115:10487-10491.

Weizmann, C., et al., "The Synthesis of α-Alkoxyisobutyric Acids and Alkyl Methacrylates from Acetonechloroform," *J. Am. Chem. Soc.* (1948) 70:1153-1158.

Willumsen, N. et al., "Enhanced Hepatic Fatty Acid Oxidation and Upregulated Carnitine Palmitoyltransferase II Gene Expression by Methyl 3-Thiaoctadeca-6,9,12,15-Tetraenoate in Rats," *J. Lipid Mediators Cell Signalling* (1997) 17:115-134.

Willumsen, N. et al., "On the Effect of 2-Deuterium- and 2-Methyl-Eicosapentaenoic Acid Derivatives on Triglyerides, Peroxisomal β-Oxidation and Platelet Aggregation in Rats," *Biochimica et Biophysica Acta* (1998) 1369:193-203.

Woodbury, D.M. & Fingl, E., "Chapter 13: Drugs Effective in the Therapy of the Epilepsies," in Basis of Therapeutics 201-226 (5th Ed. 1975).

Zeynalov, B.K. et al., "Synthesis and Investigation of Esters of Alkyl Selenium Ethanols," *Azerbajdzanskij Chimiceskij Zurnal* (1981) 5:41-43.

Cao, G. *Selected topics of pharmaceutical chemistry*. China Medical Science Press, 1993. pp. 123-125.

English translation. Cao, G. *Selected topics of pharmaceutical chemistry*. China Medical Science Press, 1993. pp. 123-125.

Office Action (Restriction Requirement) for U.S. Appl. No. 14/263,793 dated Mar. 3, 2015.

Office Action (Restriction Requirement) for U.S. Appl. No. 13/574,132, dated Jan. 20, 2015.

Silverman, R.B., The Organic Chemistry of Drug Design and Drug Action, 2nd Edition, 19-20, (Chemical Industry Press, 2008).

English Translation. Silverman, R.B., The Organic Chemistry of Drug Design and Drug Action, 2nd Edition, 19-20, (Chemical Industry Press, 2008).

English language abstract for CN 101225064.
English language abstract for EP 0 463 947.
English language abstract for JP 04-051149.
English translation of JP 11-180929.
English translation of JP 48-039001 B.

Ringbom, T, et al., "COX-2 Inhibitor Effects of Naturally Occurring and Modified Fatty Acids," *J. Nat. Prod.*(2001) 64:745-749.

Storlien, L.H., et al., "Polyunsaturated Fatty Acids, Membrane Function and Metabolic Diseases Such as Diabetes and Obesity," *Curr Opin Clin Nutr & Metab Care*(1998) 1(6):559-563.

\* cited by examiner

METHODS OF TREATMENT USING LIPID COMPOUNDS

This application is a national stage filing under 35 U.S.C. §371 of International Application No. PCT/IB2011/002925 filed on Nov. 3, 2011, which claims the benefit of U.S. Provisional Application No. 61/410,445 filed on Nov. 5, 2010. All of those applications are incorporated by reference herein in their entireties.

This application claims priority to U.S. Provisional Application No. 61/410,445, filed on Nov. 5, 2010, the disclosure of which is incorporated herein by reference in its entirety.

The present disclosure relates to methods of treating at least one disease or condition in a subject in need thereof, comprising administering to the subject a pharmaceutically effective amount of a compound of Formula (I):

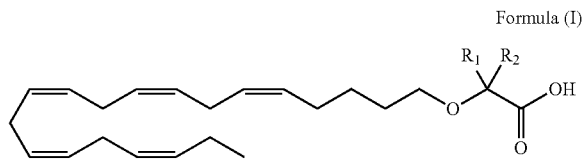

Formula (I)

or a pharmaceutically acceptable salt or ester thereof, wherein $R_1$ and $R_2$ are independently chosen from a hydrogen atom or linear, branched, and/or cyclic $C_1$-$C_6$ alkyl groups, with the proviso that $R_1$ and $R_2$ are not both hydrogen. Such diseases and/or conditions may, for example, relate to cardiovascular functions, immune functions, and/or insulin action. The present disclosure also provides for a method of treating atherosclerosis and reducing and/or slowing the progression of its development.

Dietary polyunsaturated fatty acids (PUFAs), including omega-3 fatty acids, have effects on diverse physiological processes impacting normal health and chronic diseases, such as the regulation of plasma lipid levels, cardiovascular and immune functions, insulin action, neuronal development, and visual function.

Omega-3 fatty acids, e.g., (5Z,8Z,11Z,14Z,17Z)-icosa-5,8,11,14,17-pentaenoic acid (EPA) and (4Z,7Z,10Z,13Z,16Z,19Z)-docosa-4,7,10,13,16,19-hexaenoic acid (DHA), regulate plasma lipid levels, cardiovascular and immune functions, insulin action, and neuronal development, and visual function. Omega-3 fatty acids have been shown to have beneficial effects on the risk factors for cardiovascular diseases, for example hypertension and hypertriglyceridemia (HTG), and on the coagulation factor VII phospholipid complex activity. Omega-3 fatty acids have also been shown to lower serum triglycerides, increase serum HDL cholesterol, lower systolic and diastolic blood pressure and/or pulse rate, and lower the activity of the blood coagulation factor VII-phospholipid complex.

In humans, cholesterol and triglycerides are part of lipoprotein complexes in the bloodstream that can be separated via ultracentrifugation into high-density lipoprotein (HDL), intermediate-density lipoprotein (IDL), low-density lipoprotein (LDL), and very-low-density lipoprotein (VLDL) fractions. Cholesterol and triglycerides are synthesized in the liver, incorporated into VLDL, and released into the plasma. Conditions characterized by abnormally high blood cholesterol and/or lipid values include hypercholesterolemia, hyperlipidemia (hyperlipoproteinemia), HTG, and mixed dyslipidemia. High levels of total cholesterol (total-C), LDL-C, and apolipoprotein B100 (a membrane complex for LDL and VLDL) may promote human coronary heart disease (CHD). In fact, the NCEP ATP III (National Cholesterol Education Program Adult Treatment Panel III) report specifies non-HDL cholesterol reduction as the primary treatment objective in the primary prevention of CHD.

Decreased levels of HDL-C and its transport complex, apolipoprotein A, are also associated with the development of CHD. Cardiovascular morbidity and mortality in humans correlates with the level of total-C and LDL-C, and inversely with the level of HDL-C.

Factors such as, high LDL/non-HDL cholesterol, hypertriglyceridemia (HTG), and low HDL cholesterol are features of metabolic syndrome, which represents a collection of lipid and non-lipid (e.g., hypertension) risk factors of metabolic origin. Metabolic syndrome is closely linked to a generalized metabolic disorder called insulin resistance in which the normal actions of insulin are impaired.

The NCEP ATP III (National Cholesterol Education Program Adult Treatment Panel III) recommends treating of lipid and non-lipid factors associated with metabolic syndrome, such as reducing HTG and non-HDL cholesterol, as a secondary target in the primary prevention of CHD.

The long-chain omega-3 fatty acids, EPA and DHA, are well established in the treatment of HTG and have beneficial effects upon other risk factors associated with CHD, such as hypertension and a prothrombotic state. However, due to their limited biological effects upon other cardiovascular risk factors, such as LDL, there is a need to improve their biological effects. Several research groups have studied chemical modification of omega-3 fatty acids to influence their biological effects. See, e.g., Rossmeisl et al. (*Obesity*, Jan. 15, 2009); Flock et al. (*Acta Chemica Scandinavica*, 53:436, 1999); Pitt et al. (*Synthesis*, 1240-42, 1997).

The present disclosure generally relates to a method of treating or preventing at least one disease or condition in a subject in need thereof, comprising administering to the subject a pharmaceutically effective amount of a compound of Formula (I):

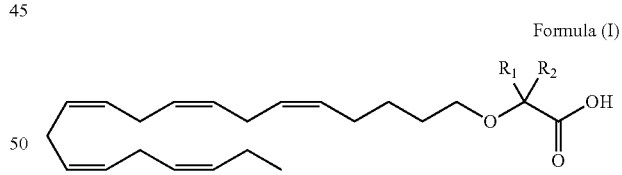

Formula (I)

or a pharmaceutically acceptable salt or ester thereof, wherein $R_1$ and $R_2$ are independently chosen from a hydrogen atom or linear, branched, and/or cyclic $C_1$-$C_6$ alkyl groups, with the proviso that $R_1$ and $R_2$ are not both hydrogen.

In at least one embodiment the at least one disease or condition is chosen from atherosclerosis, peripheral insulin resistance, a diabetic condition, or a dyslipidemic condition.

The present disclosure also includes a method of reducing atherosclerosis development in a subject in need thereof; the method comprising administering to the subject a pharmaceutically effective amount of 2-((5Z,8Z,11Z,14Z,17Z)-icosa-5,8,11,14,17-pentaen-1-yloxy)butanoic acid:

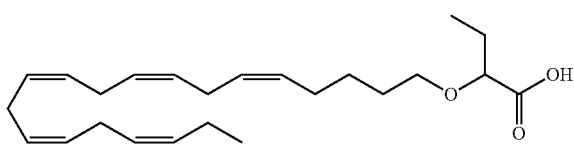

or a pharmaceutically acceptable salt or ester thereof.

DESCRIPTION

Figure 1:
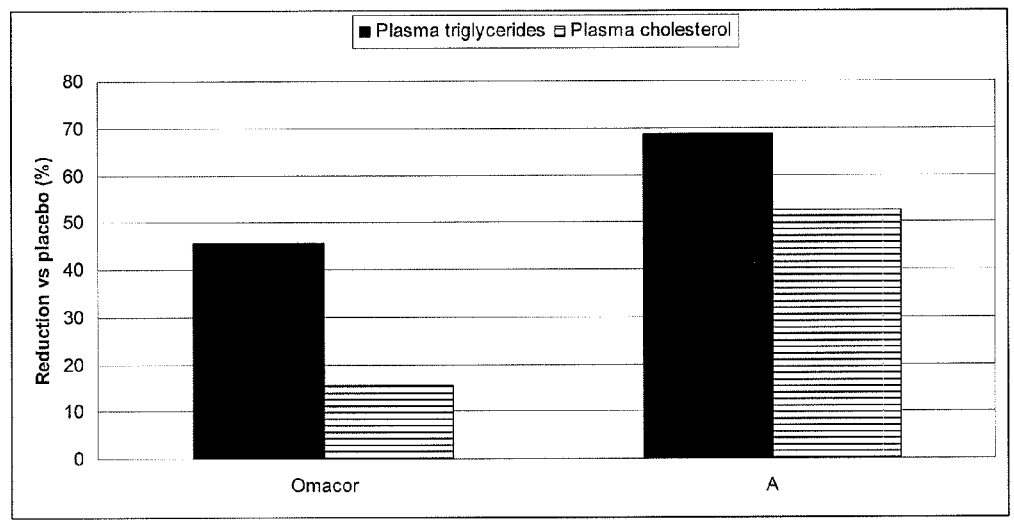
FIG. 1 shows cholesterol and triglyceride levels in APOE*3Leiden mice after administration of Compound A (0.3 mmol/kg) according to the present disclosure or Omacor™ (3.3 mmol/kg).

Particular aspects of the disclosure are described in greater detail below. The terms and definitions as used in the present application and as clarified herein are intended to represent the meaning within the present disclosure.

The singular forms "a," "an," and "the" include plural reference unless the context dictates otherwise.

The terms "approximately" and "about" mean to be nearly the same as a referenced number or value. As used herein, the terms "approximately" and "about" should be generally understood to encompass ±5% of a specified amount, frequency, or value.

The terms "treat," "treating," and "treatment" include any therapeutic application that can benefit a human or non-human mammal. Both human and veterinary treatments are within the scope of the present disclosure. Treatment may be responsive to an existing condition or it may be prophylactic, i.e., preventative.

The terms "administer," "administration," and "administering" as used herein refer to (1) providing, giving, dosing and/or prescribing by either a health practitioner or his authorized agent or under his direction a compound or composition according to the present disclosure, and (2) putting into, taking or consuming by the human patient or person himself or herself, or non-human mammal a compound or composition according to the present disclosure.

The term "pharmaceutically effective amount" means an amount sufficient to achieve the desired pharmacological and/or therapeutic effects, i.e., an amount of the disclosed compound that is effective for its intended purpose. While individual subject/patient needs may vary, the determination of optimal ranges for effective amounts of the disclosed compound is within the skill of the art. Generally, the dosage regimen for treating a disease and/or condition with the compounds presently disclosed may be determined according to a variety of factors such as the type, age, weight, sex, diet, and/or medical condition of the subject/patient.

The term "pharmaceutical composition" means a compound according to the present disclosure in any form suitable for medical use.

The compounds of Formula (I) may exist in various stereoisomeric forms, including enantiomers, diastereomers, or mixtures thereof. It will be understood that the invention encompasses all optical isomers of the compounds of Formula (I) and mixtures thereof. Hence, compounds of Formula (I) that exist as diastereomers, racemates, and/or enantiomers are within the scope of the present disclosure.

The present disclosure includes a method of treating or preventing at least one disease or condition in a subject in need thereof, comprising administering to the subject a pharmaceutically effective amount of a compound of Formula (I):

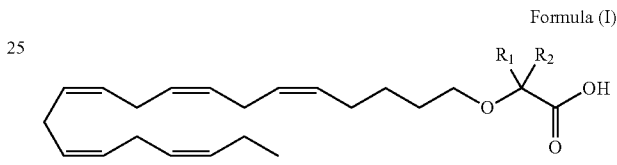

Formula (I)

or a pharmaceutically acceptable salt or ester thereof, wherein $R_1$ and $R_2$ are independently chosen from a hydrogen atom or linear, branched, and/or cyclic $C_1$-$C_6$ alkyl groups, with the proviso that $R_1$ and $R_2$ are not both hydrogen.

In at least one embodiment, $R_1$ and $R_2$ are chosen from hydrogen, methyl, ethyl, n-propyl, and isopropyl.

In at least one embodiment, the compound is present in its various stereoisomeric forms, such as an enantiomer (R or S), diastereomer, or mixtures thereof.

In at least one embodiment, the compound is present in racemic form.

In cases, where the compound according to Formula (I) is a salt of a counter-ion with at least one stereogenic center, or ester of an alcohol with at least one stereogenic center, the compound may have multiple stereocenters. In those situations, the compounds of the present disclosure may exist as diastereomers. Thus, in at least one embodiment, the compounds of the present disclosure are present as at least one diastereomer.

In at least one embodiment, the compound of the present disclosure is 2-((5Z,8Z,11Z,14Z,17Z)-icosa-5,8,11,14,17-pentaen-1-yloxy)butanoic acid:

In at least one embodiment, at least one disease or condition is chosen from atherosclerosis, peripheral insulin resistance, a diabetic condition, or a dyslipidemic condition.

In at least one embodiment blood cholesterol levels are reduced, triglycerides are reduced, HDL is increased, and/or the incidence of atherosclerosis lesions is reduced.

Compounds of Formula (I) can be prepared as described, for example, in PCT Application No. PCT/IB10/001,251 filed May 7, 2010, and according to Examples 1-11 below. Examples 1-11 are exemplary and one skilled in the art would understand how to apply these general methods to arrive at other compounds within the scope of Formula (I). Compounds of the present disclosure may be in the form of a pharmaceutically acceptable salt or ester. For example, the compounds of Formula (I) may be in the form of esters, such as a phospholipid, a triglyceride, a 1,2-diglyceride, a 1,3 diglyceride, a 1-monoglyceride, or a 2-monoglyceride.

Salts suitable for the present disclosure include, but are not limited to, salts of $NH_4^+$; metal ions such as $Li^+$, $Na^+$, $K^+$, $Mg^{2+}$, or $Ca^{2+}$; a protonated primary amine such as tert-butyl ammonium, (3S,5S,7S)-adamantan-1-ammonium, 1,3-dihydroxy-2-(hydroxymethyl)propan-2-ammonium, a protonated aminopyridine (e.g., pyridine-2-ammonium); a protonated secondary amine such as diethylammonium, 2,3,4,5,6-pentahydroxy-N-methylhexan-1-ammonium, N-ethylnaphthalen-1-ammonium, a protonated tertiary amine such as 4-methylmorpholin-4-ium, and a protonated guanidine such as amino((4-amino-4-carboxybutyl)amino)methaniminium or a protonated heterocycle such as 1H-imidazol-3-ium. Additional examples of suitable salts include salts of a diprotonated diamine such as ethane-1,2-diammonium or piperazine-1,4-diium. Other salts according to the present disclosure may comprise protonated Chitosan:

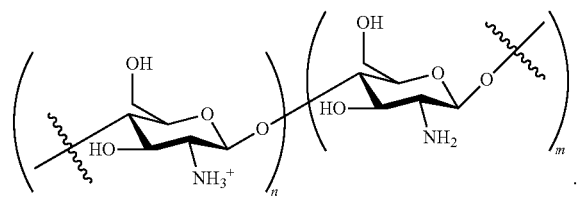

The present disclosure provides for methods of treating and/or preventing at least one disease or condition in a subject in need thereof, comprising administering to the subject a pharmaceutically effective amount of a compound of Formula (I). The subject may be a human or a non-human mammal. The compounds presently disclosed may be administered as a medicament, such as in a pharmaceutical composition.

The composition presently disclosed may comprise at least one compound of Formula (I) and optionally at least one non-active pharmaceutical ingredient, i.e., excipient. Non-active ingredients may solubilize, suspend, thicken, dilute, emulsify, stabilize, preserve, protect, color, flavor, and/or fashion active ingredients into an applicable and efficacious preparation, such that it may be safe, convenient, and/or otherwise acceptable for use. Examples of excipients include, but are not limited to, solvents, carriers, diluents, binders, fillers, sweeteners, aromas, pH modifiers, viscosity modifiers, antioxidants, extenders, humectants, disintegrating agents, solution-retarding agents, absorption accelerators, wetting agents, absorbents, lubricants, coloring agents, dispersing agents, and preservatives. Excipients may have more than one role or function, or may be classified in more than one group; classifications are descriptive only and are not intended to be limiting. In some embodiments, for example, the at least one excipient may be chosen from corn starch, lactose, glucose, microcrystalline cellulose, magnesium stearate, polyvinylpyrrolidone, citric acid, tartaric acid, water, ethanol, glycerol, sorbitol, polyethylene glycol, propylene glycol, cetylstearyl alcohol, carboxymethylcellulose, and fatty substances such as hard fat or suitable mixtures thereof. In some embodiments, the compositions presently disclosed comprise at least one compound of Formula (I) and at least one pharmaceutically acceptable antioxidant, e.g., tocopherol and 3-BHA.

The compositions presently disclosed may be formulated in oral administration forms, e.g., tablets or gelatine soft or hard capsules, The dosage form can be of any shape suitable for oral administration, such as spherical, oval, ellipsoidal, cube-shaped, regular, and/or irregular shaped. Conventional formulation techniques known in the art, may be used to formulate the compounds according to the present disclosure. In some embodiments, the composition may be in the form of a gelatin capsule or a tablet.

A suitable daily dosage of a compound of Formula (I) may range from about 5 mg to about 3 g. For example, in some embodiments, the daily dose ranges from about 5 mg to about 1 g, from about 10 mg to about 1 g, from about 10 mg to about 800 mg, from about 10 mg to about 600 mg, from about 10 mg to about 500 mg, from about 50 mg to about 500 mg. In at least one embodiment, the daily dose ranges from about 50 mg to about 500 mg. The compounds may be administered, for example, once, twice, or three times per day. In at least one embodiment, the compound of Formula (I) is administered in an amount ranging from about 10 mg to about 500 mg per dose. In at least one embodiment, the compound of Formula (I) is administered once per day.

The compounds of Formula (I) disclosed herein may be administered to treat and/or prevent at least one disease, condition or risk factor associated with coronary heart disease (CHD). For example, in some embodiments, at least one disease or condition is chosen from atherosclerosis; peripheral insulin resistance and/or a diabetic condition such as type 2 diabetes; a dyslipidemic condition such as hypertriglyceridemia (HTG), elevated total cholesterol, elevated non-HDL cholesterol, elevated LDL-cholesterol, elevated Apo B, low HDL-cholesterol, primary hypercholesterolemia (heterozygous familial and nonfamilial), mixed dyslipidemia (Fredrickson Types IIa and IIb), primary dysbetalipoproteinemia (Fredrickson Type III); metabolic syndrome; obesity or an overweight condition; and a fatty liver disease such as a non-alcoholic fatty liver disease (NAFLD).

In at least one embodiment, at least one disease or condition is atherosclerosis. For example, the present disclosure further encompasses a method of reducing and/or slowing the progression of atherosclerosis development. The methods presently disclosed may, for example, reduce at least one of plasma insulin, blood glucose, and serum triglycerides in a subject in need thereof. The present disclosure also provides for a method of treating and/or preventing at least one of elevated triglyceride levels, elevated VLDL/LDL cholesterol levels and low HDL cholesterol levels in a subject in need thereof.

The present inventors have found that compounds of Formula (I), such as 2-((5Z,8Z,11Z,14Z,17Z)-icosa-5,8,11,14,17-pentaen-1-yloxy)butanoic acid, have remarkably good pharmaceutical activity. The compounds of Formula (I) presently disclosed may exhibit improved biological activity compared to naturally occurring omega-3 fatty acids, such as EPA and DHA.

In some embodiments, for example, compounds of Formula (I) may exhibit comparable or higher biological activity than other cholesterol-lowering pharmaceutical agents, e.g., fenofibrate, without the side-effects associated with fibrates such as myopathy, gallstones, and dyspepsia.

EXAMPLES

The present disclosure may be further described by the following non-limiting examples, in which standard techniques known to the skilled chemist and techniques analogous to those described in these examples may be used where appropriate. It is understood that the skilled artisan will envision additional embodiments consistent with the disclosure provided herein.

Unless otherwise stated, reactions were carried out at room temperature, typically in the range between 18-25° C. with solvents of HPLC grade under anhydrous conditions. Evaporations were carried out by rotary evaporation in vacuo. Column chromatography was performed by the flash procedure on silica gel. Nuclear magnetic resonance (NMR) shift values were recorded on a Bruker Avance DPX 200 or 300 instrument with peak multiplicities described as follows: s, singlet; d, doublet; dd, double doublet; t, triplet; q, quartet; p, pentet; m, multiplett; br, broad. Mass spectra were recorded with a G1956A mass spectrometer (electrospray, 3000 V) switching positive and negative ionization mode. Reported yields are illustrative and do not necessarily represent the maximum yield attainable.

Example 1

Preparation of tert-butyl 2-((5Z,8Z,11Z,14Z,17Z)-icosa-5,8,11,14,17-pentaen-1-yloxy)butanoate

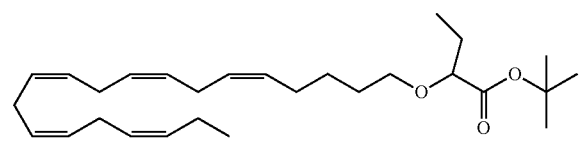 [SMILES: CC/C=C\C/C=C\C/C=C\C/C=C\C/C=C\CCCCOC(CC)C(=O)OC(C)(C)C]

Tetrabutylammonium chloride (0.55 g, 1.98 mmol) was added to a solution of (5Z,8Z,11Z,14Z,17Z)-icosa-5,8,11,14,17-pentaen-1-ol, (3.50 g, 12.1 mmol) in toluene (35 mL) at ambient temperature under nitrogen. An aqueous solution of sodium hydroxide (50% (w/w), 11.7 mL) was added under vigorous stirring at room temperature, followed by t-butyl 2-bromobutyrate (5.41 g, 24.3 mmol). The resulting mixture was heated to 50° C. and additional t-butyl 2-bromobutyrate was added after 1.5 hours (2.70 g, 12.1 mmol), 3.5 hours (2.70 g, 12.1 mmol) and 4.5 hours (2.70 g, 12.1 mmol) and stirred for 12 hours in total. After cooling to room temperature, ice water (25 mL) was added and the resulting two phases were separated. The organic phase was washed with a mixture of NaOH (5%) and brine, dried (MgSO$_4$), filtered and concentrated. The residue was purified by flash chromatography on silica gel using increasingly polar mixtures of heptane and ethyl acetate (100:0→95:5) as eluent. Concentration of the appropriate fractions afforded 1.87 g (36% yield) of the title compound as an oil. $^1$H NMR (300 MHz, CDCl3): δ 0.85-1.10 (m, 6H), 1.35-1.54 (m, 11H), 1.53-1.87 (m, 4H), 1.96-2.26 (m, 4H), 2.70-3.02 (m, 8H), 3.31 (dt, 1H), 3.51-3.67 (m, 2H), 5.10-5.58 (m, 10H).

Example 2

Preparation of 2-((5Z,8Z,11Z,14Z,17Z)-icosa-5,8,11,14,17-pentaenyloxy)butanoic acid (Compound A)

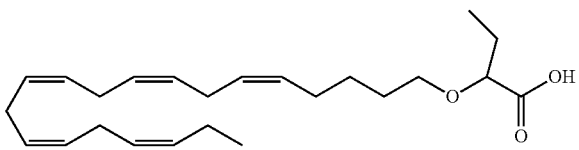 [SMILES: CC/C=C\C/C=C\C/C=C\C/C=C\C/C=C\CCCCOC(CC)C(=O)O]

tert-Butyl 2-((5Z,8Z,11Z,14Z,17Z)-icosa-5,8,11,14,17-pentaen-1-yloxy)butanoate (19.6 g, 45.5 mmol) was dissolved in dichloromethane (200 mL) and placed under nitrogen. Trifluoroacetic acid (50 mL) was added and the reaction mixture was stirred at room temperature for one hour. Water was added and the aqueous phase was extracted twice with dichloromethane. The combined organic extract was washed with brine, dried (Na$_2$SO$_4$), filtered and concentrated. The residue was subjected to flash chromatography on silica gel using increasingly polar mixtures of heptane, ethyl acetate and formic acid (90:10:1→80:20:1) as eluent. Concentration of the appropriate fractions afforded 12.1 g (71% yield) of the title compound as an oil. $^1$H-NMR (300 MHz, CDCl$_3$): δ 0.90-1.00 (m, 6H), 1.50 (m, 2H), 1.70 (m, 2H), 1.80 (m, 2H), 2.10 (m, 4H), 2.80-2.90 (m, 8H), 3.50 (m, 1H), 3.60 (m, 1H), 3.75 (t, 1H), 5.30-5.50 (m, 10H); MS (electro spray): 373.2 [M-H]$^-$.

Example 3

Preparation of (4S,5R)-3-((S)-2-((5Z,8Z,11Z,14Z,17Z)-icosa-5,8,11,14,17-pentaenyloxy)butanoyl)-4-methyl-5-phenyloxazolidin-2-one and (4S,5R)-3-((R)-2-((5Z,8Z,11Z,14Z,17Z)-icosa-5,8,11,14,17-pentaenyloxy)butanoyl)-4-methyl-5-phenyloxazolidin-2-one

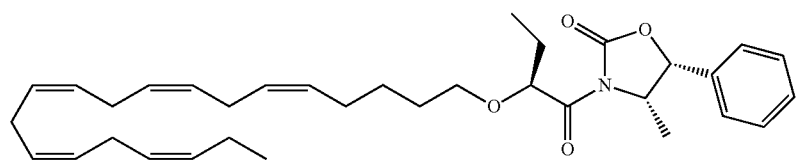

-continued

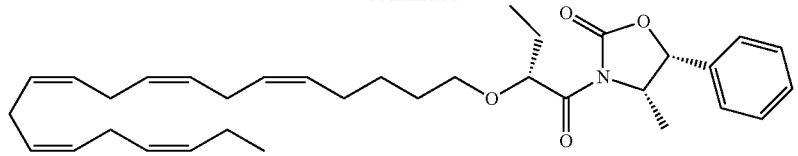

DMAP (1.10 g, 8.90 mmol) and DCC (1.90 g, 9.30 mmol) were added to a mixture of 2-((5Z,8Z,11Z,14Z,17Z)-icosa-5,8,11,14,17-pentaenyloxy)butanoic acid (3.20 g, 8.50 mmol) in dry dichloromethane (100 mL) held at 0° C. under nitrogen. The resulting mixture was stirred at 0° C. for 20 minutes. (4S,5R)-4-methyl-5-phenyloxazolidin-2-one (1.50 g, 8.50 mmol) was added and the resulting turbid mixture was stirred at ambient temperature for five days. The mixture was filtrated and concentrated under reduced pressure to give a crude product containing the desired product as a mixture of two diastereomers. The residue was purified by flash chromatography on silica gel using 15% ethyl acetate in heptane as eluent. The two diastereomers were separated and the appropriate fractions were concentrated. (4S,5R)-3-((S)-2-((5Z,8Z,11Z,14Z,17Z)-icosa-5,8,11,14,17-pentaenyloxy)butanoyl)-4-methyl-5-phenyloxazolidin-2-one eluted first and was obtained in 1.1 g (40% yield) as an oil. (4S,5R)-3-((R)-2-((5Z,8Z,11Z,14Z,17Z)-icosa-5,8,11,14,17-pentaenyloxy)butanoyl)-4-methyl-5-phenyloxazolidin-2-one was obtained in 0.95 g (34% yield) as an oil.

(4S,5R)-3-((S)-2-((5Z,8Z,11Z,14Z,17Z)-icosa-5,8,11,14,17-pentaenyloxy)butanoyl)-4-methyl-5-phenyloxazolidin-2-one (E1)

$^1$H-NMR (300 MHz, CDCl$_3$): δ 0.90 (d, 3H), 1.00 (t, 3H), 1.07 (t, 3H), 1.45-1.57 (m, 2H), 1.62-1.76 (m, 3H), 1.85-1.95 (m, 1H), 2.05-2.15 (m, 4H), 2.87 (m, 8H), 3.39 (m, 1H), 3.57 (m, 1H), 4.85-4.92 (m, 2H), 5.30-5.45 (m, 10H), 5.75 (d, 1H), 7.32 (m, 2H), 7.43 (m, 3H).

(4S,5R)-3-((R)-2-((5Z,8Z,11Z,14Z,17Z)-icosa-5,8,11,14,17-pentaenyloxy)butanoyl)-4-methyl-5-phenyloxazolidin-2-one (E2)

$^1$H-NMR (300 MHz, CDCl$_3$): δ 0.98 (d, 3H), 0.99 (t, 3H), 1.08 (t, 3H), 1.40-1.52 (m, 2H), 1.55-1.75 (m, 3H), 1.80-1.90 (m, 1H), 2.05-2.15 (m, 4H), 2.84 (m, 8H), 3.39 (m, 1H), 3.56 (m, 1H), 4.79 (pent, 1H), 4.97 (dd, 1H), 5.30-5.45 (m, 10H), 5.71 (d, 1H), 7.33 (m, 2H), 7.43 (m, 3H).

Example 4

Preparation of (S)-2-((5Z,8Z,11Z,14Z,17Z)-icosa-5,8,11,14,17-pentaenyloxy)butanoic acid (Compound B)

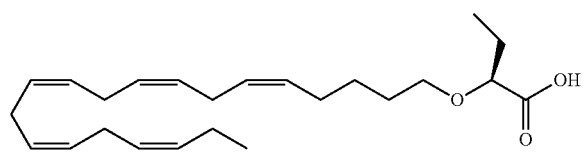 [SMILES: CC/C=C\C/C=C\C/C=C\C/C=C\C/C=C\CCCCO[C@@H](CC)C(=O)O]

Hydrogen peroxide (35% in water, 0.75 mL, 8.54 mmol) and lithium hydroxide monohydrate (0.18 g, 4.27 mmol) was added to a solution of (4S,5R)-3-((S)-2-((5Z,8Z,11Z,14Z,17Z)-icosa-5,8,11,14,17-pentaenyloxy)butanoyl)-4-methyl-5-phenyloxazolidin-2-one (1.10 g, 2.13 mmol) in tetrahydrofuran (12 mL) and water (4 mL) held at 0° C. under nitrogen. The reaction mixture was stirred at 0° C. for 30 minutes. 10% Na$_2$SO$_{3(aq)}$ (30 mL) was added, the pH was adjusted to ~2 with 2M HCl and the mixture was extracted twice with heptane (30 mL). The combined organic extract was dried (Na$_2$SO$_4$), filtered and concentrated. The residue was subjected to flash chromatography on silica gel using increasingly polar mixtures of heptane and ethyl acetate (98:8→1:1) as eluent. Concentration of the appropriate fractions afforded 0.48 g (60% yield) of the title compound as an oil. $^1$H-NMR (300 MHz, CDCl$_3$): δ 0.90-1.00 (m, 6H), 1.48 (m, 2H), 1.65 (m, 1.85 (m, 2H), 2.10 (m, 4H), 2.80-2.90 (m, 8H), 3.55 (m, 1H), 3.60 (m, 1H), 3.88 (t, 1H), 5.35-5.45 (m, 10H); MS (electro spray): 373.3 [M-H]$^-$; [□]$_D$+37° (c=0.104, ethanol).

Example 5

Preparation of (R)-2-((5Z,8Z,11Z,14Z,17Z)-icosa-5,8,11,14,17-pentaenyloxy)butanoic acid (Compound C)

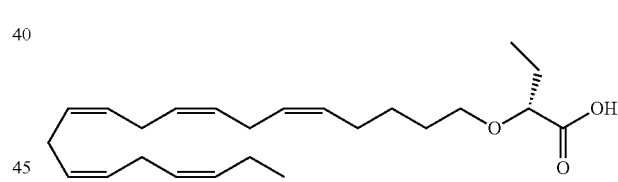

Hydrogen peroxide (35% in water, 0.65 mL, 7.37 mmol) and lithium hydroxide monohydrate (0.15 g, 3.69 mmol) was added to a solution of (4S,5R)-3-((R)-2-((5Z,8Z,11Z,14Z,17Z)-icosa-5,8,11,14,17-pentaenyloxy)butanoyl)-4-methyl-5-phenyloxazolidin-2-one (0.95 g, 1.84 mmol) in tetrahydrofuran (12 mL) and water (4 mL) held at 0° C. under nitrogen. The reaction mixture was stirred at 0° C. for 30 minutes. 10% Na$_2$SO$_{3(aq)}$ (30 mL) was added, the pH was adjusted to ~2 with 2M HCl and the mixture was extracted twice with heptane (30 mL). The combined organic extract was dried (Na$_2$SO$_4$), filtered and concentrated. The residue was subjected to flash chromatography on silica gel using increasingly polar mixtures of heptane and ethyl acetate (98:8→50:50) as eluent. Concentration of the appropriate fractions afforded 0.19 g (29% yield) of the title compound as an oil. $^1$H-NMR (300 MHz, CDCl$_3$): δ 0.90-1.00 (m, 6H), 1.48 (m, 2H), 1.65 (m, 2H), 1.85 (m, 2H), 2.10 (m, 4H), 2.80-2.90 (m, 8H), 3.55 (m, 1H), 3.60 (m, 1H), 3.88 (t, 1H), 5.35-5.45 (m, 10H); MS (electro spray): 373.3 [M-H]⁻; [□]$_D$ −31° (c=0.088, ethanol).

Example 6

Preparation of tert-butyl 2-((5Z,8Z,11Z,14Z,17Z)-icosa-5,8,11,14,17-pentaenyloxy)propanoate

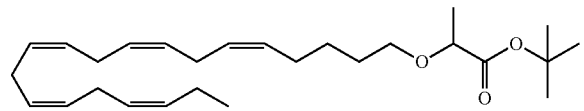 [SMILES: CC/C=C\C/C=C\C/C=C\C/C=C\C/C=C\CCCCOC(C)C(=O)OC(C)(C)C]

A mixture of (5Z,8Z,11Z,14Z,17Z)-icosa-5,8,11,14,17-pentaen-1-ol, (1.00 g, 3.47 mmol), tetrabutylammonium chloride (0.24 g, 0.87 mmol) and t-butyl □-bromo propionate (3.62 g, 17.3 mmol) was dissolved in toluene (36 mL) and placed under nitrogen. An aqueous solution of sodium hydroxide (50%, 8 mL) was added slowly under vigorous stirring and the resulting mixture was stirred at ambient temperature for twenty hours. Water was added and the mixture was extracted three times with ether. The combined organic extract was washed with brine, dried (Na₂SO₄), filtered and concentrated. The residue was purified by flash chromatography on silica gel using 2% ethyl acetate in heptane as eluent. Concentration of the appropriate fractions afforded 1.40 g (90% yield) of the title compound as an oil. ¹H-NMR (300 MHz, CDCl₃): δ 0.95 (t, 3H), 1.41 (d, 3H), 1.48 (s, 9H), 1.48-1.66 (m, 4H), 2.05 (m, 4H), 2.83 (m, 8H), 3.35 (m, 1H), 3.55 (m, 1H), 3.79 (q, 1H), 5.32-5.44 (m, 10H).

Example 7

Preparation of 2-((5Z,8Z,11Z,14Z,17Z)-icosa-5,8,11,14,17-pentaenyloxy)propanoic acid

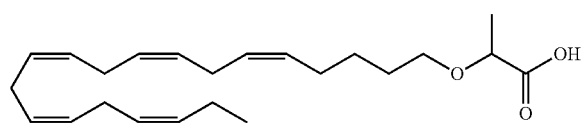 [SMILES: CC/C=C\C/C=C\C/C=C\C/C=C\C/C=C\CCCCOC(C)C(=O)O]

Trifluoroacetic acid (2 mL) was added to a solution of 2-((5Z,8Z,11Z,14Z,17Z)-icosa-5,8,11,14,17-pentaenyloxy)propanoate (1.40 g, 3.36 mmol) in dichloromethane (10 mL) held under nitrogen and the reaction mixture was stirred at room temperature for three hours. Diethyl ether (50 mL) was added and the organic phase was washed with water (30 mL), dried (Na₂SO₄) and concentrated. The residue was subjected to flash chromatography on silica gel using increasingly polar mixtures of heptane, ethyl acetate and formic acid (95:5:0.25→80:20:1) as eluent. Concentration of the appropriate fractions afforded 0.67 g of slightly impure product. This material was dissolved in heptane (15 mL), washed three times with water (5 mL), dried (Na₂SO₄), filtered and concentrated to afford 0.50 g (41% yield) of the title compound as an oil. ¹H-NMR (300 MHz, CDCl₃): δ 0.99 (t, 3H), 1.40-1.48 (m, 5H), 1.67 (m, 2H), 2.09 (m, 4H), 2.80-2.60 (m, 8H), 3.53 (m, 2H), 4.01 (q, 1H), 5.31-5.47 (m, 10H); MS (electro spray): 359.2 [M-H]⁻.

Example 8

Preparation of tert-butyl 2-((5Z,8Z,11Z,14Z,17Z)-icosa-5,8,11,14,17-pentaenyloxy)-2-methylpropanoate

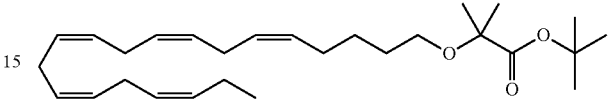

A mixture of (5Z,8Z,11Z,14Z,17Z)-icosa-5,8,11,14,17-pentaen-1-ol, (0.83 g, 3.14 mmol), tetrabutylammonium chloride (0.24 g, 0.85 mmol) and t-butyl □-bromo isobutyrate (3.50 g, 15.7 mmol) was dissolved in toluene (15 mL) and placed under nitrogen. An aqueous solution of sodium hydroxide (50%, 5 mL) was added slowly under vigorous stirring at room temperature. The resulting mixture was heated to 60° C. and stirred for six hours. The mixture was cooled, added water and extracted three times with ether. The combined organic extract was washed with brine, dried (Na₂SO₄), filtered and concentrated. The residue was purified by flash chromatography on silica gel using a gradient of 5-10% ethyl acetate in heptane as eluent. Concentration of the appropriate fractions afforded 0.60 g (44% yield) of the title compound as an oil. MS (electro spray): 453.3 [M+Na]⁺.

Example 9

Preparation of 2-((5Z,8Z,11Z,14Z,17Z)-icosa-5,8,11,14,17-pentaenyloxy)-2-methylpropanoic acid

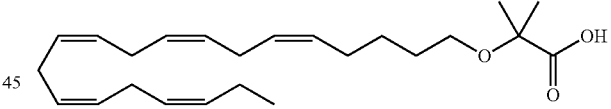

Trifluoroacetic acid (5 mL) was added to a solution of tert-butyl 2-((5Z,8Z,11Z,14Z,17Z)-icosa-5,8,11,14,17-pentaenyloxy)-2-methylpropanoate (600 mg, 1.39 mmol) in dichloromethane (20 mL) under nitrogen and the reaction mixture was stirred at room temperature for two hours. Water was added and the aqueous phase was extracted twice with dichloromethane. The combined organic extract was washed with brine, dried (Na₂SO₄), filtered and concentrated. The residue was purified by flash chromatography on silica gel using a mixture of heptane, ethyl acetate and formic acid (80:20:1) as eluent. The appropriate fractions were concentrated and the residue (135 mg) was purified further by flash chromatography on silica gel using a gradient of 5-10% of a mixture of ethyl acetate and formic acid (95:5) in heptane as eluent. Concentration of the appropriate fractions afforded 80 mg slightly impure product. This material was dissolved in heptane (5 mL), washed twice with water (5 mL), dried (Na₂SO₄), filtered and concentrated to afford 40 mg (8% yield) of the title compound as an oil. ¹H-NMR (300 MHz, CDCl₃): δ 0.99 (t, 3H), 1.47 (s, 6H), 1.64 (m, 2H), 2.07 (m, 4H), 2.81-2.88 (m, 8H), 3.46 (t, 2H), 5.29-5.44 (m, 10H); MS (electro spray): 373.3 [M-H]⁻.

Example 10

Preparation of tert-butyl 2-ethyl-2-((5Z,8Z,11Z,14Z, 17Z)-icosa-5,8,11,14,17-pentaen-1-yloxy)butanoate

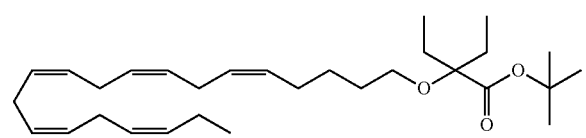 [SMILES: CC/C=C\C/C=C\C/C=C\C/C=C\C/C=C\CCCCOC(CC)(CC)C(=O)OC(C)(C)C]

tert-Butyl 2-((5Z,8Z,11Z,14Z,17Z)-icosa-5,8,11,14,17-pentaen-1-yloxy)butanoate (480 mg, 1.11 mmol) was added dropwise over 30 minutes to a solution of lithium diisopropylamine (LDA) (2.0 M, 750 µL, 1.50 mmol) in dry tetrahydrofuran (10 mL) held at −70° C. under nitrogen. The reaction mixture was stirred for 30 minutes. Ethyl iodide (312 mg, 2.00 mmol) was added in one portion and the resulting mixture was warmed to ambient temperature during 1 hour. The reaction mixture was stirred at ambient temperature for 17 hours. The mixture was poured into saturated NH$_4$Cl (aq.) (50 mL) and extracted with heptane (2×50 mL). The combined organic phases was washed successively with brine (50 mL), 0.25 M HCl (50 mL) and brine (50 mL), dried (MgSO$_4$), filtered and concentrated. The residue was purified by flash chromatography on silica gel using increasingly polar mixtures of heptane and ethyl acetate (100:0→95:5) as eluent. Concentration of the appropriate fractions afforded 343 mg (67% yield) of the title compound as an oil. $^1$H NMR (300 MHz, CDCl3): δ 0.84 (t, 6H), 0.99 (td, 3H), 1.35-1.55 (m, 11H), 1.54-1.69 (m, 2H), 1.68-1.87 (m, 4H), 1.99-2.24 (m, 4H), 2.74-2.99 (m, 8H), 3.31 (t, 2H), 5.23-5.52 (m, 10H); MS (electro spray): 401.3 [M−1]⁻.

Example 11

Preparation of 2-ethyl-2-((5Z,8Z,11Z,14Z,17Z)-icosa-5,8,11,14,17-pentaen-1-yloxy)butanoic acid

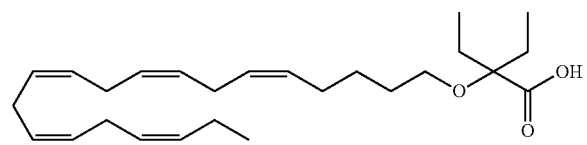 [SMILES: CC/C=C\C/C=C\C/C=C\C/C=C\C/C=C\CCCCOC(CC)(CC)C(=O)O]

A mixture of formic acid (5 ml) and tert-butyl 2-ethyl-2-((5Z,8Z,11Z,14Z,17Z)-icosa-5,8,11,14,17-pentaen-1-yloxy) butanoate (250 mg, 0.55 mmol) was stirred vigorously under nitrogen at room temperature for 4.5 hours. The formic acid was removed in vacuo. The residue was purified by flash chromatography on silica gel using increasingly polar mixtures of heptane and ethyl acetate (100:0→80:20) as eluent. Concentration of the appropriate fractions afforded 163 mg (74% yield) of the title compound as an oil. $^1$H NMR (300 MHz, CDCl3): δ 0.86 (t, 6H), 0.99 (t, 3H), 1.36-1.57 (m, 2H), 1.68 (dd, 2H), 1.73-1.98 (m, 4H), 2.11 (tt, 4H), 2.70-3.01 (m, 8H), 3.39 (t, 2H), 5.20-5.56 (m, 10H). MS (electrospray): 481.4 [M+Na]⁺.

Example 12

Evaluation of PPAR activation in vitro

Compounds (A)-(C) and a positive control were tested at six different concentrations in duplicate:

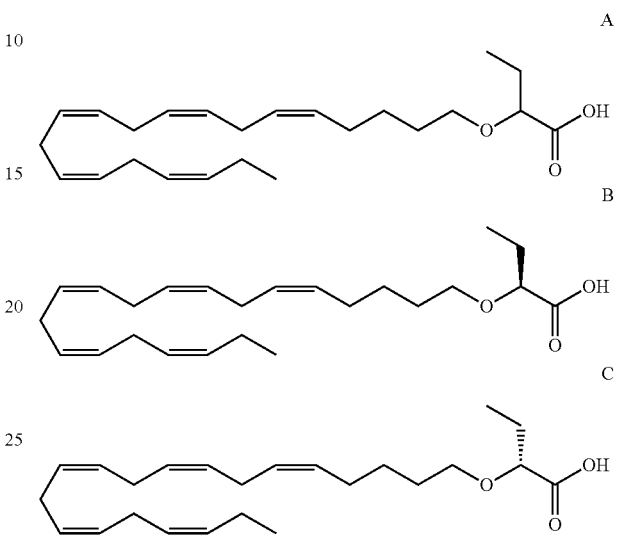

The positive controls were GW7647 (PPAR□), GW501516 (PPAR□) and rosiglitazone (PPAR□). The efficacy of the controls were set to 100%.

Assays were carried out in vitro using mammalian-one-hybrid assays (M1H) comprising GAL4-DNA binding domain-PPAR-LBD fusion constructs in conjunction with 5×GAL4-sites driven *Photinus pyralis* luciferase reporter constructs in transiently transfected HEK293 cells. The cells were transfected 4-6 hours and grown overnight before compounds were added. Compound incubation was 16-20 hours. *Renilla reniformis* luciferase, driven by a constitutive promoter, was included as internal control to improve experimental accuracy. Results appear in Table 1.

TABLE 1

| PPAR activation in vitro. | | | | | | |
|---|---|---|---|---|---|---|
| | PPAR□ | | PPAR□ | | PPAR□ | |
| Compound | EC$_{50}$ | Efficacy | EC$_{50}$ | Efficacy | EC$_{50}$ | Efficacy |
| Pos. ctr. | 0.45 nM | 100% | 0.33 nM | 100% | 22 nM | 100% |
| A | 307 nM | 82% | inactive | inactive | 806 nM | 22% |
| B | 405 nM | 86% | inactive | inactive | 644 nM | 27% |
| C | 167 nM | 54% | inactive | inactive | 515 nM | 25% |

Example 13

Evaluation of the effects on in vivo lipid metabolism in a dyslipidemic mouse model (APOE*3Leiden transgenic mice)

The dyslipidemic mouse model has proven to be representative of the human situation with respect to plasma lipoprotein levels and responsiveness to hypolipidemic drugs, such as statins and fibrates, and nutritional intervention. In addition, depending on the level of plasma cholesterol, APOE*3Leiden mice develop atherosclerotic lesions in the aorta resembling those found in humans with respect to cellular composition and morphological and immunohistochemical characteristics.

Female APOE*3Leiden mice were put on a semi-synthetic Western-type diet (WTD, 15% cocoa butter, 40% sucrose and 0.25% cholesterol; all w/w). With this diet the plasma cholesterol level reached mildly elevated levels of approximately 12-15 mmol/l. After a 4 week run-in period the mice were sub-divided into groups of 10 mice each, matched for plasma cholesterol, triglycerides and body weight (t=0).

Test substances were administered orally as admix to the Western-type diet. To facilitate mixing of the compounds, sunflower oil was added to a total oil volume of 10 mL/kg diet. Compound (A) of Example 2 above was tested at 0.3 mmol/kg bw/day. A reference compound of omega-3 acid ethyl esters (Omacor™/Lovaza™) was tested at 3.3 mmol/kg bw/day. At t=0 and 4 weeks, blood samples were taken after a 4 hour-fast to measure plasma cholesterol and triglycerides. Results are shown in FIG. 1.

Example 14

Evaluation of the effects on in vivo lipid metabolism in a dyslipidemic mouse model (APOE*3Leiden.CETP transgenic mice)

The APOE*3Leiden.CETP transgenic mouse is a model where the human cholesterol ester transfer protein has been introduced to the APOE*3Leiden transgenic mouse. This results in a more human-like lipoprotein profile and is well-suited for testing the effects of drugs on plasma HDL and triglyceride levels.

Female APOE*3Leiden.CETP mice were put on a semi-synthetic modified Western-type diet (0.15% cholesterol and 15% saturated fat, all w/w). With this diet the plasma cholesterol level reaches moderately elevated levels of about 13-15 mmol/l and triglyceride levels of approximately 3 mmol/l. After a 4 week run-in period, the mice were sub-divided into groups of 6 mice each, matched primarily for plasma cholesterol, triglycerides and body weight and secondarily for HDL-cholesterol (t=0).

Figure 2:
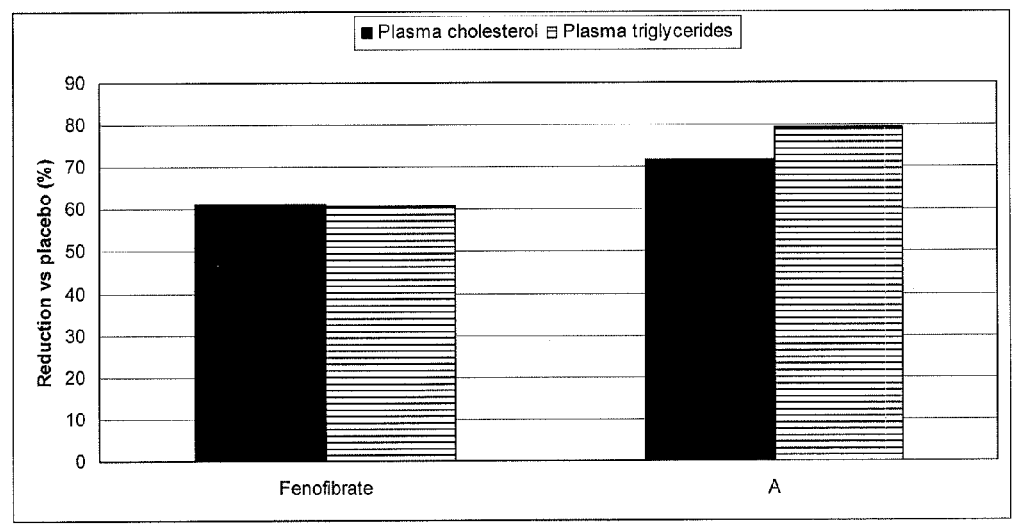
FIG. 2 shows cholesterol and triglyceride levels in APOE*3Leiden.CETP mice after administration of Compound A according to the present disclosure or fenofibrate.
Figure 3:
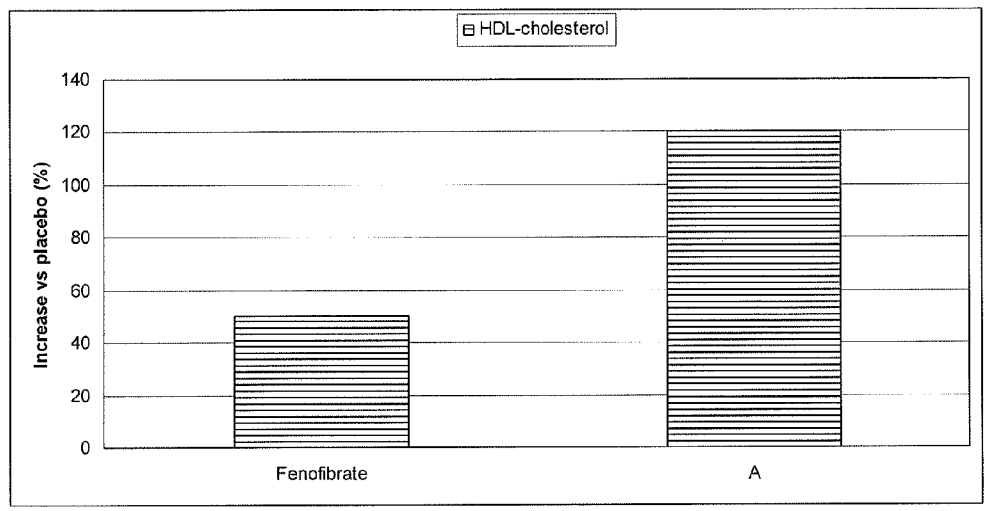
FIG. 3 shows HDL levels in APOE*3Leiden.CETP mice after administration of Compound A according to the present disclosure or fenofibrate.

Test substances were administered orally as admix to the Western-type diet. At t=0 and 4 weeks blood samples were taken after a 4 hour-fast to measure plasma cholesterol, HDL-cholesterol and triglycerides. Compound (A) of Example 2 above was tested at 0.18 mmol/kg bw/day. The reference (Fenofibrate) was tested at 10 mg/kg bw/day. Results are shown in FIGS. 2 and 3.

Example 15

Evaluation of the effects on in vivo atherosclerosis development in a mouse model (APOE*3Leiden.CETP transgenic mice)

The APOE*3Leiden.CETP transgenic mouse has proven to be representative of the human situation with respect to plasma lipoprotein levels and its responsiveness to hypolipidemic drugs (like statins, fibrates etc.) and nutritional intervention. APOE*3Leiden.CETP mice develop atherosclerotic lesions in the aorta resembling those found in humans with respect to cellular composition and morphological and immunohistochemical characteristics.

Female APOE*3Leiden.CETP mice were put on a Western-type diet (WTD) with 0.15% cholesterol and 15% saturated fat; resulting in plasma cholesterol levels of about 13-15 mM. After a 3 week run-in period on the WTD, the mice were sub-divided into 4 groups of 15 mice, control (no treatment), Compound A of Example 2 above, fenofibrate and a low-cholesterol diet. The groups were matched for body weight, plasma total cholesterol (TC), HDL cholesterol (HDL-C) and triglycerides (TG) after 4 h fasting (t=0).

The test substances were administered orally as admix to the Western-type diet. To facilitate the mixing of the compounds sunflower oil was added to a total oil volume of 10 mL/kg diet. Compound (A) was tested at initially at 0.1 mmol/kg bw/day and reduced to 0.04 mmol/kg bw/day at 4 weeks; the initial dose was based on a prior dose-finding study to establish the required dosage that would reduce VLDL/LDL cholesterol by 25-30%. The fenofibrate dose was initially 10 mg/kg bw/day, and later reduced to 4.2 mg/kg bw/day to parallel reductions in VLDL/LDL cholesterol induced by Compound A.

At t=0 and t=17 weeks, blood samples were taken after a 4 hour-fast period to measure plasma cholesterol and triglycerides. Atherosclerosis development in aortic root (total lesion area) was measured at sacrifice.

The results for total cholesterol (mM), HDL cholesterol (mM), lesion area ($\mu m^2 \times 1000$) and undiseased segments (%) are shown in FIGS. 4, 5, 6, and 7, respectively.

Figure 4:
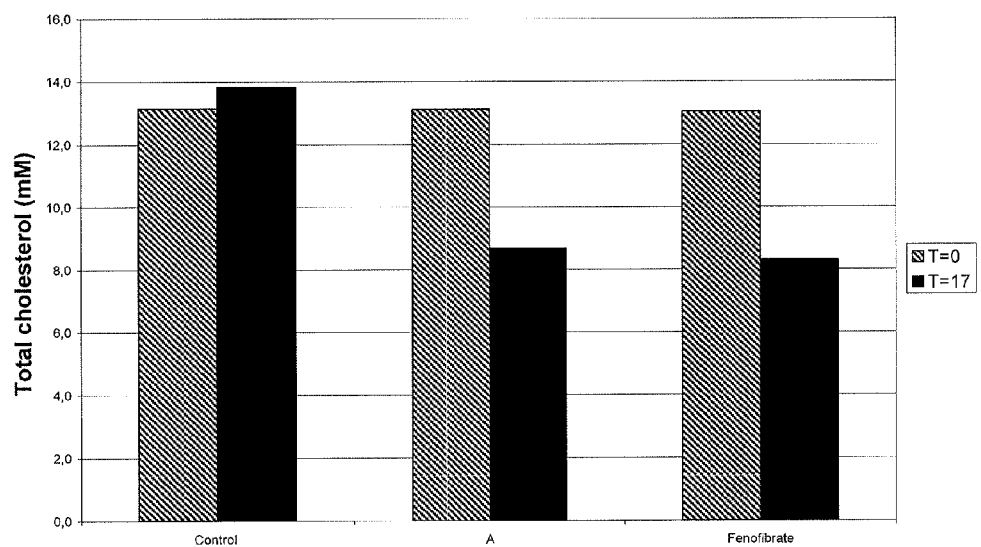
FIG. 4 shows total cholesterol levels in APOE*3Leiden CETP mice after administration of Compound A according to the present disclosure, fenofibrate, or a negative control.
Figure 5:
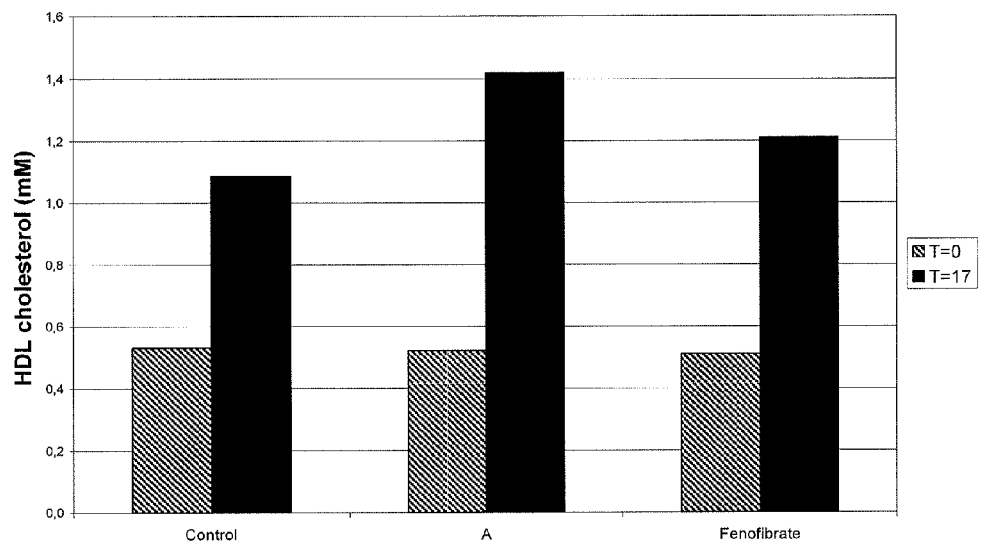
FIG. 5 shows HDL levels in APOE*3Leiden CETP mice after administration of Compound A according to the present disclosure, fenofibrate, or a negative control.
Figure 6:
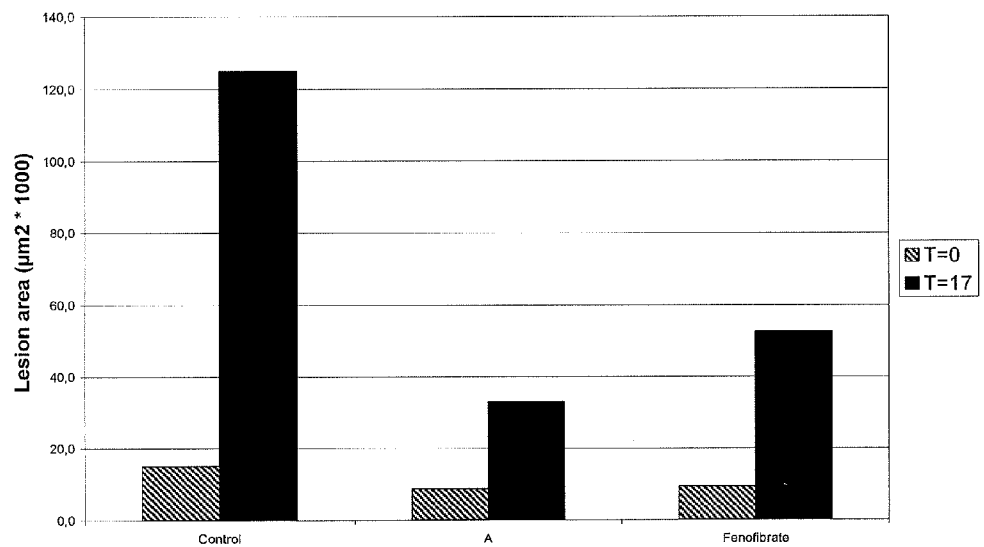
FIG. 6 shows diseased lesion area in APOE*3Leiden CETP mice after administration of Compound A according to the present disclosure, fenofibrate, or a negative control.
Figure 7:
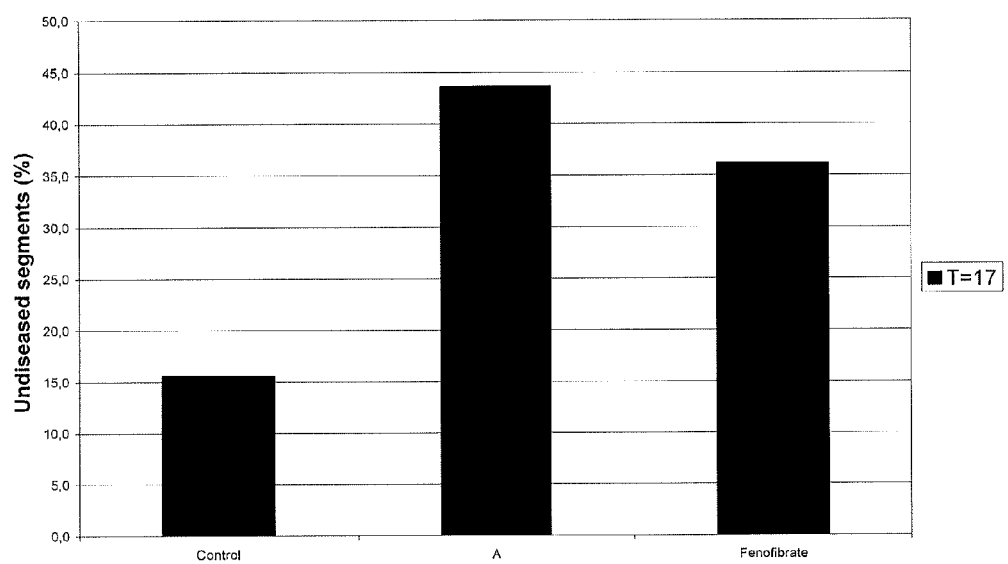
FIG. 7 shows undiseased lesion area in APOE*3Leiden CETP mice after administration of Compound A according to the present disclosure, fenofibrate, or a control.

As shown in FIGS. 4 and 5, Compound A significantly decreased total cholesterol (p<0.001) and significantly increased HDL cholesterol (p<0.003) as compared to control. Compound A also significantly decreased lesion area (p<0.003) and undiseased segments (p<0.003) as compared to control (FIGS. 6 and 7).

These results suggest that Compound A favorably influences lipid profiles and inhibits the development of atherosclerosis in APOE*3Leiden.CETP transgenic mice.

The invention claimed is:

1. A method of treating elevated Apo B in a subject in need thereof, comprising administering to the subject a pharmaceutically effective amount of a compound of Formula (I):

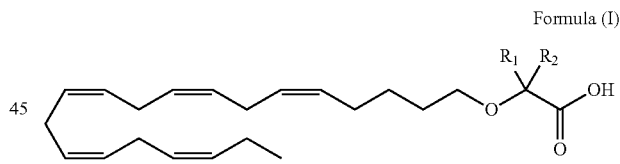

Formula (I)

or a pharmaceutically acceptable salt or ester thereof,
wherein $R_1$ and $R_2$ are independently chosen from a hydrogen atom or linear, branched, and/or cyclic $C_1$–$C_5$ alkyl groups, with the proviso that $R_1$ and $R_2$ are not both hydrogen.

2. The method according to claim 1, wherein the compound is present in the form of an enantiomer, diastereomer, or mixture thereof.

3. The method according to claim 1, wherein $R_1$ and $R_2$ are chosen from a hydrogen atom, a methyl group, an ethyl group, an n-propyl group, and an isopropyl group.

4. The method according to claim 2, wherein the compound is present in its R form.

5. The method according to claim 2, wherein the compound is present in its S form.

6. The method according to claim 2, where the compound is present in racemic form.

7. The method according to claim 1, wherein $R_1$ is hydrogen and $R_2$ is ethyl and the formula is

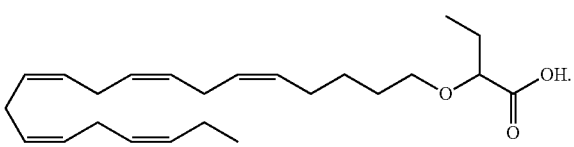 [SMILES: CC/C=C\C/C=C\C/C=C\C/C=C\C/C=C\CCCCOC(CC)C(=O)O]

8. The method according to claim 7, wherein the compound is present in its S and/or R form represented by the formulas:

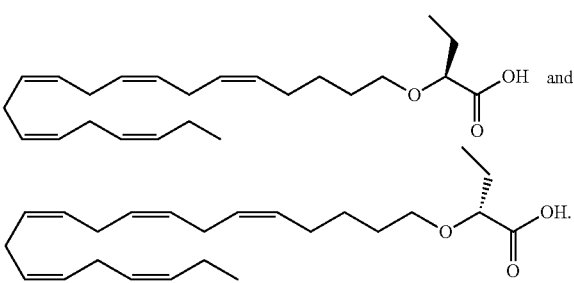

9. The method according to claim 1, wherein the pharmaceutically effective amount of the compound of Formula (I) ranges from about 5 mg to about 3 g per dose.

10. The method according to claim 1, wherein the subject is a human.

11. The method according to claim 1, wherein the compound is administered once daily.

12. The method according to claim 1, wherein the compound is formulated as a pharmaceutical composition for oral administration.

13. The method according to claim 12, wherein the pharmaceutical composition is in the form of a gelatin capsule or a tablet.

14. The method according to claim 13, wherein the pharmaceutical composition further comprises at least one binder, excipient, diluent, or any combinations thereof.

15. The method according to claim 12, wherein the pharmaceutical composition further comprises an antioxidant.

16. The method according to claim 15, wherein the antioxidant is tocopherol or BHA.

17. A method of reducing elevated Apo B levels, in a subject in need thereof, the method comprising administering to the subject a pharmaceutically effective amount of 2-((5Z,8Z,11Z,14Z,17Z)-icosa-5,8,11,14,17-pentaen-1-yloxy)butanoic acid:

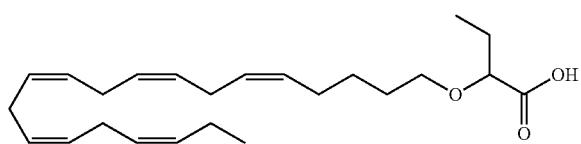 [SMILES: CC/C=C\C/C=C\C/C=C\C/C=C\C/C=C\CCCCOC(CC)C(=O)O]

or a pharmaceutically acceptable salt or ester thereof.

18. The method according to claim 17, wherein the pharmaceutically-effective amount of 2-((5Z,8Z,11Z,14Z,17Z)-icosa-5,8,11,14,17-pentaen-1-yloxy)butanoic acid ranges from about 5 mg to about 3 g per dose.

19. The method according to claim 18, wherein 2-((5Z,8Z,11Z,14Z,17Z)-icosa-5,8,11,14,17-pentaen-1-yloxy)butanoic acid is administered once daily.

* * * * *